(12) United States Patent
Puranik et al.

(10) Patent No.: US 9,891,200 B2
(45) Date of Patent: Feb. 13, 2018

(54) METAL COORDINATION COMPLEX FOR DETECTION OF VAPORS AND ANIONS AND PROCESS FOR THE PREPARATION THEREOF

(71) Applicant: Council of Scientific and Industrial Research, New Delhi (IN)

(72) Inventors: Vedavati Gururaj Puranik, Pune (IN); Rajesh Ghanshyam Gonnade, Pune (IN); Rupesh Liladhar Gawade, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/507,554

(22) PCT Filed: Aug. 28, 2015

(86) PCT No.: PCT/IN2015/050101
§ 371 (c)(1),
(2) Date: Feb. 28, 2017

(87) PCT Pub. No.: WO2016/056027
PCT Pub. Date: Apr. 14, 2016

(65) Prior Publication Data
US 2017/0284986 A1    Oct. 5, 2017

(30) Foreign Application Priority Data
Aug. 29, 2014 (IN) .......... 2463/DEL/2014

(51) Int. Cl.
*C07F 1/08* (2006.01)
*G01N 31/22* (2006.01)
(Continued)

(52) U.S. Cl.
CPC .......... *G01N 31/22* (2013.01); *C07F 1/08* (2013.01); *G01N 21/783* (2013.01); *G01N 33/182* (2013.01); *C07B 2200/13* (2013.01)

(58) Field of Classification Search
CPC .......... C07F 1/08
(Continued)

(56) References Cited

U.S. PATENT DOCUMENTS 8,008,090 B2    8/2011    Lefebvre et al.

FOREIGN PATENT DOCUMENTS

WO    WO-2016056027    4/2016

OTHER PUBLICATIONS

Chen, Q. et al.: Conformational isomerism of a flexible fluorinated bis-pyridinecarboxamide ligand in the structural direction of two distinct layered Cu coordination polymers. Inorganic Chem. Commun., vol. 11, pp. 1371-1374, 2008.*

(Continued)

*Primary Examiner* — Charanjit Aulakh
(74) *Attorney, Agent, or Firm* — Schwegman Lundberg & Woessner, P.A.

(57) ABSTRACT

The present invention discloses novel multi-action copper complexes which are used for reversible vapochromic detection of polar solvents as well as anion sensing in both aqueous and non-aqueous media.

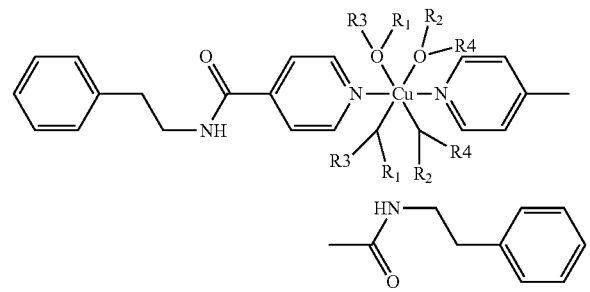

Formula X

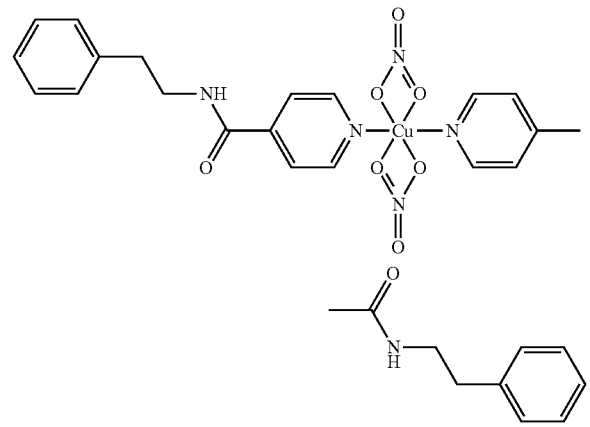

Formula 1

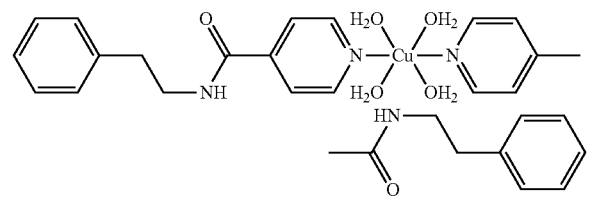

Formula 2

9 Claims, 11 Drawing Sheets

(51) Int. Cl.
*G01N 21/78* (2006.01)
*G01N 33/18* (2006.01)

(58) Field of Classification Search
USPC .......................................................... 546/2
See application file for complete search history.

(56) References Cited

OTHER PUBLICATIONS

Feng, Liang, et al., "Colorimetric sensing of anions in water using ratiometric indicator-displacement assay", Analytica Chimica Acta, vol. 743, Sep. 19, 2012, pp. 1-8, (Sep. 19, 2012), 1-8.

Royzman, Dmitry E., et al., "Structure, Luminescence, and Vapochromism of Bridged Cationic Copper(I) Dimers and Polymers", Journal of Inorganic and Organometallic Polymers and Materials, Jan. 2014, vol. 24, Issue 1, pp. 66-77, (Jan. 2014), 66-77.

Tetilla, Marta Aquado, et al., "Colorimetric response to anions by a "robust" copper(II) complex of a [9]aneN3 pendant arm derivative: CN- and I- selective sensing", Chem. Commun., 2011, (13) 47, 3805-3807, (Feb. 2, 2011), 3805-3807.

Zhang, Xu, et al., "Luminescence vapochromism in solid materials based on metal complexes for detection of volatile organic compounds (VOCs)", J. Mater. Chem., 2012, 22, 11427-11441, (Apr. 13, 2012), 11427-11441.

"International Application No. PCT/IN2015/050101, International Search Report and Written Opinion dated Jan. 22, 2016", (Jan. 22, 2016), 8 pgs.

"International Application No. PCT/IN2015/050101, Statement Under Article 19 dated Mar. 15, 2015", (Mar. 15, 2015), 6 pgs.

Akhuli, Bidyut, et al., "Selective recognition of sulphate in a Cu(II) assisted 1D polymer of a simple pentafluorophenyl substituted pyridyl-urea via second sphere coordination", Dalton Trans., 2013, 42, 5818, (Feb. 5, 2013), 5818-5825.

Mendy, John S., et al., "Anion Recognition and Sensing by a New Macrocyclic Dinuclear Copper(II) Complex: A Selective Receptor for Iodide", Inorg Chem. Aug. 16, 2010; 49(16): 7223-7225, (Aug. 16, 2010), 11 pgs.

* cited by examiner

Scheme 1

METAL COORDINATION COMPLEX FOR DETECTION OF VAPORS AND ANIONS AND PROCESS FOR THE PREPARATION THEREOF

PRIORITY CLAIM TO RELATED APPLICATIONS

This application is a U.S. national stage application filed under 35 U.S.C. §371 from International Application Serial No. PCT/IN2015/050101, which was filed 28 Aug. 2015, and published as WO2016/056027 on 14 Apr. 2016, and which claims priority to India Application No. 2463/DEL/2014, filed 29 Aug. 2014, which applications and publication are incorporated by reference as if reproduced herein and made a part hereof in their entirety, and the benefit of priority of each of which is claimed herein.

FIELD OF THE INVENTION

The present invention relates to a multi-action metal coordination complex of formula X and the process for the synthesis of said complex. Particularly, the present invention relates to multi-action metal coordination complexes which are useful for reversible vapochromic detection of polar solvents and for anion sensing in both aqueous and non-aqueous media.

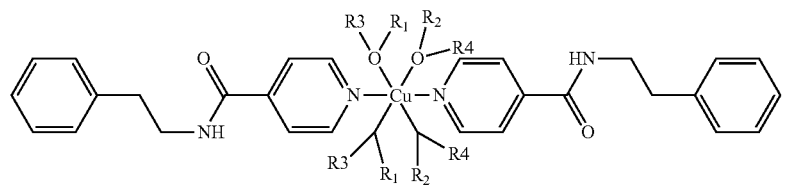

Formula (X)

Wherein,
$R_1$, $R_2$, $R_3$ and $R_4$ is selected from H or $R_1$ and $R_3$ jointly represent NO group and $R_2$ and $R_4$ jointly represent NO group.

BACKGROUND OF THE INVENTION

Anion recognition continues to be a major research goal for many supramolecular chemistry groups around the world. As the field matures there is an increasing emphasis on synthetic receptors that operate in aqueous solution. This is because most of the important biomolecular targets such as peptides, nucleotides, phospholipids, and carbohydrates are anionic compounds. However, anion recognition in water is an extremely challenging task for a number of reasons. For a start, anions are strongly hydrated and any complexation process that involves anion dehydration will likely have to pay a large energetic penalty. Common anions, such as halide ions (fluoride, chloride, bromide, and iodide), sulphide, sulphate, chromate, phosphate, oxalate, and nitrite, play vital roles in the environment, industry and biology. Some of these common anions are essential for our life. Anions play an important role in health, food, biomedical and defense industries. Their release in the environment cause hazardous effects to living system by drastically affecting the food and water quality. This necessitates the development of highly sensitive anion sensor materials for monitoring the presence of these toxic pollutants. There is an immense upsurge in last 2-3 decades in designing and synthesizing suitable anion sensors. Classical methods for detection of these hazardous anions which include spectroscopic, electrochemical and chromatographic are very expensive and time consuming. Therefore, in recent years, the investigation on anions sensing methodologies is focused on exploring rapid, versatile, cost-effective and optical detectors.

Vapochromic materials suitable for sensing volatile organic compounds (VOCs) by the alteration of auro- and metallophilic attractions have attracted considerable attention. Whereas these systems often include metallophilic Pt—Pt, Au—Tl, Au—Au, and Au—Ag interactions, complexes with Au—Cu metal centers are generally less common, and such vapochromic complexes are understood to have not been reported.

Vapochromic materials have recently been incorporated in chemical sensor devices. For example, [Au—(PPh$_2$C (CSSAuC$_6$F$_5$)PPh$_2$Me)$_2$][ClO$_4$] has been used in the development of an optical fiber VOC sensor. A vapochromic light emitting diode and a vapochromic photodiode have also been built using tetrakis(p-dodecylphenylisocyano) platinum tetranitroplatinate and bis(cyanide)-bis(p-dodecylphenylisocyanide)platinum(II), respectively.

Anion sensors are broadly classified into two main categories based on their anion binding mode, 1) Binding via non-covalent interactions: anion sensor recognizes or detects anions through donor acceptor non-covalent interactions which include electrostatic, hydrophilic, hydrophobic, hydrogen bonding and π . . . π interactions; 2) Linkage through covalent bond: the analyte directly ligates to the metal based coordination complexes through coordinate bond. Designing non-covalently interacting anion sensing receptors suffer major challenges for their usage in aqueous media due to strong water-anion interaction through H-bonding. Higher energy requirement of receptor binding to hydrated anions also makes it an unfavorable process. Covalently bonded metal based receptors can overcome this problem by strongly interacting with anions through coordinate bond. The binding process can be monitored by visible changes in colour or changes in fluorescence intensity.

Article titled "Anion Recognition and Sensing by a New Macrocyclic Dinuclear Copper (II) Complex: A Selective Receptor for Iodide" by J S Mendy et al. published in *Inorg. Chem.*, 2010, 49 (16), pp 7223-7225 reports a macrocyclic dinuclear copper complex, [Cu$_2^{II}$(1)Br$_3$(H$_2$O)]Br synthesized and characterized by X-ray crystallography, in which the macrocycle is folded to form a bowl-shaped cavity. The sensing ability of the receptor was studied for halides by UV-VIS spectroscopy in water-acetonitrile (1:3 v/v) and water. The article mentioned reported a macrocyclic dinuclear complex [Cu$_2$ II(1)Br$_3$(H$_2$O)]Br, which showed a strong affinity only for iodide anion. However, the media used for binding studies is not completely aqueous but the mixture of aprotic solvent $CH_3CN$ and water (3:1). Complete aqueous media (100% water) may inhibit efficient binding with metal binding sites that are not the case for $C_1/C_2$. Additionally reported macrocyclic compound is completely soluble in media used for the study so it is not the solid state detection and has limited applicability for its use for removing anions.

Article titled "Colorimetric sensing of anions in water using ratiometric indicator-displacement assay" by L Feng et al. published in Analytica Chimica Acta, 2012, 743, pp 1-8 reports use of colorimetric indicator-displacement assay (IDA) array for the determination of ten anions in water. The color changes in IDA array provide facile identification of these anions with no misclassification. The sensor array consists of different combinations of colorimetric indicators and metal cations. The colorimetric indicators chelate with metal cations, forming the color changes.

U.S. Pat. No. 8,008,090B2 discloses vaprochromic coordination polymers useful for analyte detection. The vapochromism may be observed by visible color changes, changes in luminescence, and/or spectroscopic changes in the infrared (IR) signature. In one particular embodiment a new class of [Metal(CN)$_2$]-based coordination polymers with vapochromic properties is described, such as Cu[Au(CN)$_2$]$_2$ and Zn[Au(CN)$_2$]$_2$ polymers, wherein said analyte is a volatile organic compound. The compound show differential behaviour when exposed to a variety of solvent vapours e.g. DMSO, water, etc. However, they have not been explored for detection of analytes in a solution state Article titled "Structure, Luminescence, and Vapochromism of Bridged Cationic Copper(I) Dimers and Polymers" by D E Royzman et al. published in *Journal of Inorganic and Organometallic Polymers and Materials*, January 2014, 24 (1), pp 66-77 reports the dimeric complex of Cu(I) [Cu$_2$(PPh$_3$)$_4$(MeCN)$_2$(Bpy)](BF$_4$)$_2$ (1a, Bpy=4,4'-dipyridyl) self-assembles in $CH_2Cl_2$ or acetone and shows intense photoluminescence (excitation $\lambda_{max}$=356 nm, emission $\lambda_{max}$=486 nm, φ=0.47).

Article titled "Colorimetric response to anions by a "robust" copper(II) complex of a [9]aneN$_3$ pendant arm derivative: CN$^-$ and I$^-$ selective sensing" by MA Tetilla et al. published in Chem Commun (Camb), 2011, 47 (13), pp 3805-3807 report a 1:1 complex [Cu(L)](BF$_4$)$_2$.MeCN (1) of the tetradentate ligand 1-(2-quinolinylmethyl)-1,4,7-triazacyclononane (L) selectively changes its colour in the presence of CN$^-$ in $H_2O$ and MeCN (without undergoing decomplexation from the macrocyclic ligand). The same complex in MeCN assumes different colours in the presence of CN$^-$ or I$^-$. However sensing in solid state and completely aqueous media (100% water) is not investigated.

Article titled "Luminescence vapochromism in solid materials based on metal complexes for detection of volatile organic compounds (VOCs)" by X Zhang et al. published in *J. Mater. Chem.*, 2012, 22, 11427-11441 reports that vapour-triggered luminescence colour changes are mostly relevant to a variation of weak interactions such as metal-solvent bonds, metallophilic contacts, π-π stacking, hydrogen bonding, host-guest affinity or reversible isomerization etc.

It has now become essential to find highly sensitive, broad spectrum, cost-effective anion sensors which can detect wide range of anions in aqueous as well as non-aqueous media via optical detection methods. The feasibility of anions sensors as solid state detector makes it more convenient to use in the sensing devices. Solid state thin film of sensors after recognizing anions can transduce signal which can be detected by optical, electrochemical and electrical methods. Metal based anion receptors have shown enigmatic potential for their uses as anion detector. Metals can 1) act as a part of the colorimetric or luminescent reporter group; 2) they can provide template for anion induced self-assembly and 3) provide anion binding site due to Lewis acidity. Tailor made designing of structurally dynamic 1D or 2D coordination framework where metal provides site for analyte interaction which in turn offers switchable flexibility thereby rendering efficient solid state sensing method. Therefore, there is a need for designing novel coordination complexes for effective vapochromic and anion sensing property.

OBJECTIVE OF THE INVENTION

The main objective of the present invention is to provide a multi-action copper coordination complex of formula X.

Another objective of the present invention is to provide a process for the synthesis of multi-action copper complex of formula X.

Yet another objective of the present invention is to provide multi-action copper complex useful for reversible vapochromic detection of polar solvents and for anion sensing in both aqueous and non-aqueous media.

SUMMARY OF THE INVENTION

Accordingly, present invention provides a complex of formula X

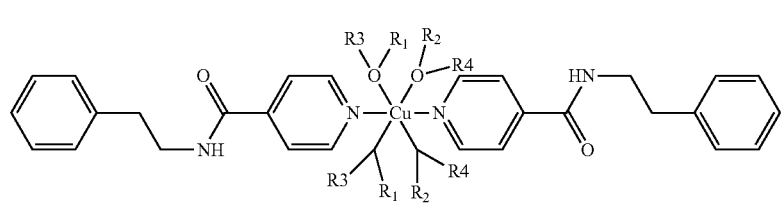

Formula X wherein,

R$_1$, R$_2$, R$_3$ and R$_4$ is selected from H or R$_1$ and R$_3$ jointly represent NO group and R$_2$ and R$_4$ jointly represent NO group.

In an embodiment of the present invention, representative compound of formula X are

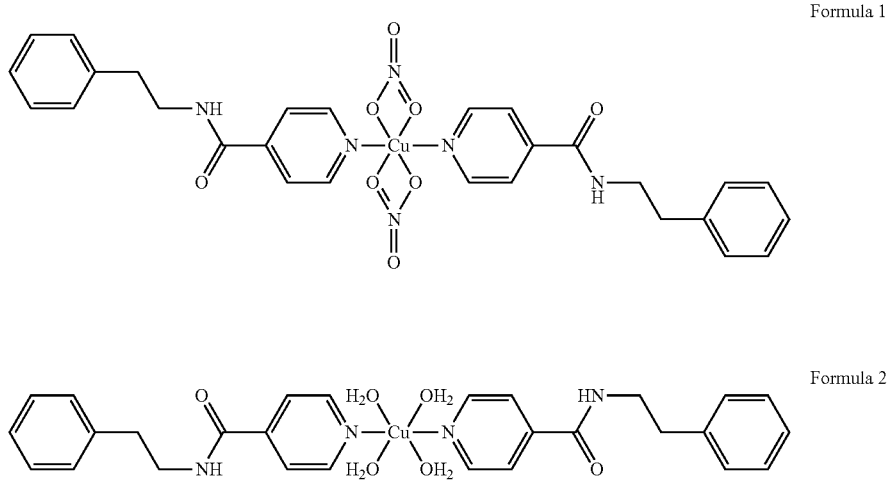

Formula 1

Formula 2

In another embodiment of the present invention, said complex shows vapochromic behavior for polar solvent within a minute.

In yet another embodiment of the present invention, the polar solvent is selected from the group consisting of methanol, ethanol, acetone, dimethylformamide, dimethyl sulfoxide and Tetrahydrofuran.

In yet another embodiment of the present invention, said complex showed colour change in the solid state.

In yet another embodiment, present invention provides a process for the synthesis of complex of formula X and the said process comprising the steps of:

a. adding triethylamine ($Et_3N$) to a stirred solution of isonicotinoylchloride in dichloromethane (DCM) followed by adding 2-phenethylamine with stirring for period in the range of 7 to 8 hrs at room temperature in the range of 20 to 30° C. to obtain N-phenethylisonicotinamide ligand;
b. adding methanolic solution of N-phenethylisonicotinamide ligand of step (a) to $Cu(NO_3)_2 \cdot 3H_2O$ with stirring followed by refluxing, filtering and separating the solution in two parts;
c. crystallizing one part of the solution as obtained in step (b) in methanol to yield blue coloured needle shaped crystals of complex of formula (1) and crystallizing the second part of the solution as obtained in step (b) in a MeOH-water mixture to obtain green coloured plates of complex of formula (2);
d. adding water to the blue crystals of formula 1 to obtain green crystal of formula 2 and suspending green crystals of formula 2 in methanol to yield blue crystals of formula 1.

In yet another embodiment, present invention provides a process for selective, naked eye detection of anions in aqueous and non-aqueous medium using complex of formula X comprising the steps of:

i. suspending the powder of complex of formula X in aqueous solution of tetrabutylammonium (TBA) or ammonium salts, alkali metal salts of various anions in the ratio 20:1 followed by observing the change in colour of the solid sample.

In yet another embodiment of the present invention, the anions are selected from the group consisting of chloride, bromide, nitro, thiocynate, formate and acetate.

In yet another embodiment of the present invention, said process may comprises co-grinding the powder of complex of formula X with tetrabutylammonium (TBA) or ammonium salts, alkali metal salts of various anions for period in the range of 2 to 5 minutes followed by observing the change in colour of the solid sample.

BRIEF DESCRIPTION OF THE DRAWINGS

Scheme 1 represents steps for the preparation of compound of formula X.

FIG. 3(*a*) and FIG. 3(*b*) represent crystal packing diagram and cartoon illustration of H-bonded sheet framework viewed along 1D of Complex of formula 2 ($Cu\_H_2O$), FIG. 3(*c*) represent intermediate step where analyte vapours of polar solvents diffuse through lattice and interact non-covalently.

FIG. 3(*d*) and FIG. 3(*e*) represent crystal packing diagram and cartoon illustration of H-bonded sheet framework viewed along ID of Complex of formula 1 (Cu MeOH).

FIG. 5(*a*) and FIG. 5(*b*) represent cartoon illustration and crystal packing diagram of H-bonded sheet framework viewed along 1D chain of complex of formula 1 (Cu_MeOH). FIG. 5(*d*) represents cartoon illustrations whereas FIG. 5(*c*) and FIG. 5(*e*) represents crystal packing diagrams of H-bonded sheet framework viewed along 1D chain of complexes of formula 3 and 4 after chloride and bromide anions coordination respectively, FIG. 5(*f*) and 5(*g*) shows molecular diagrams of repeating unit of complexes of formula 3 (Cu_Cl) and 4 (Co_Br).

FIG. 6(*a*) and FIG. 6(*b*) represent cartoon illustration and crystal packing diagram of H-bonded sheet framework viewed along 1D chain of complex of formula 1 (Cu_MeOH), FIG. 6(c) and FIG. 6(d) represent cartoon illustration and crystal packing diagram of H-bonded sheet framework viewed along 1D layer of complex of formula 5 (Cu_SCN) after thiocyanate anion coordination, FIG. 6(e) molecular diagram of repeating unit of complex of formula 5.

FIG. 7(a) and FIG. 7(b) represent cartoon illustration and crystal packing diagram of H-bonded sheet framework viewed along 1D chain of complex of formula 1 (Cu_MeOH). FIG. 7(c) and FIG. 7(d) represent cartoon illustration and crystal packing diagram of H-bonded sheet framework viewed along 1D chain of complex 6 after formate anion coordination, FIG. 7(e) molecular diagram of repeating unit of complex of formula 6 (Cu_Formate).

FIG. 8(a) and FIG. 8(b) represent cartoon illustration and crystal packing diagram of H-bonded sheet framework viewed along 1D chain of complex of formula 1 (Cu_MeOH), FIG. 8(c) and FIG. 8(d) represent cartoon illustration and crystal packing diagram of H-bonded sheet framework viewed along 1D chain of complex of formula 7 after acetate anion coordination, FIG. 8(e) molecular diagram of repeating unit of complex of formula 7 (Cu_Acetate).

FIG. 9(b) acetate and formate anion sensing FIG. 9(c) chloride and bromide anion detection, FIG. 9(d) thiocyanate anion sensing and FIG. 9(e) nitrite anion detection.

FIG. 10(a) represents simulated (1a) and experimental (1b) PXRD pattern of complex of formula 1 (Cu_MeOH). FIG. 10(b) represents simulated (2a) and experimental (2b) PXRD pattern of complex of formula 2 (Cu_$H_2O$). FIG. 10(c) represents simulated (3a) and experimental (3b) PXRD pattern of complex of formula 3 (Cu_Cl) and FIG. 10(d) represents simulated (4a) and experimental (4b) PXRD pattern of complex of formula 4 (Cu_Br).

FIG. 11(a) represents simulated (5a) and experimental (5b) PXRD pattern of complex of formula 5 (Cu_SCN), FIG. 11(b) represents simulated (6a) and experimental (6b) PXRD pattern of complex of formula 6 (Cu_formate). FIG. 11(c) represents simulated (7a) and experimental (7b) PXRD pattern of complex of formula 7 (Cu_acetate). FIG. 11(d) represents experimental (8) PXRD pattern of complex of formula 8 (Cu_nitrite).

DETAILED DESCRIPTION OF THE INVENTION

Figure 1:
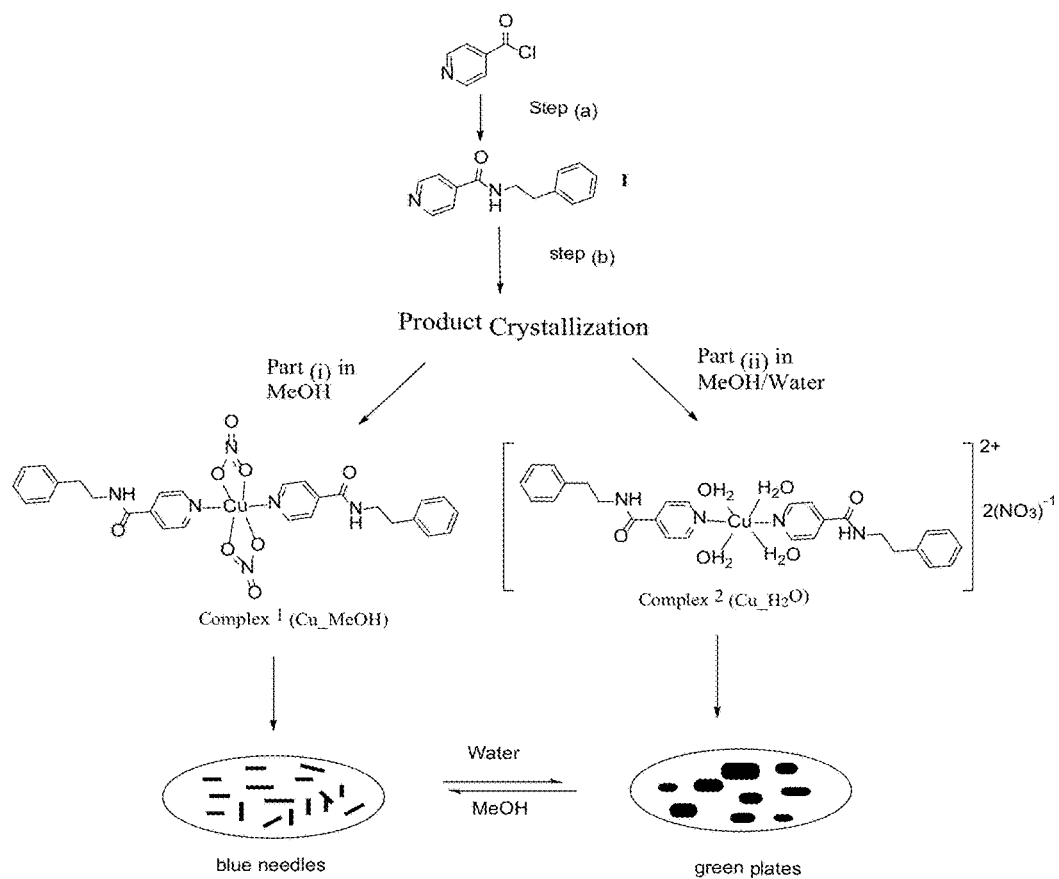
FIG. 1: Vapochromism experiment: (1) crystallization chamber with powder of green crystals of compound ($Cu\_H_2O$, 2), (2) closed assembly containing solvent and powder of green crystals of 2, (3) powder turned blue (Cu_MeOH, 1) on exposure to solvent vapours, (4) recording of UV absorption/reflectance spectra.
Figure 1:
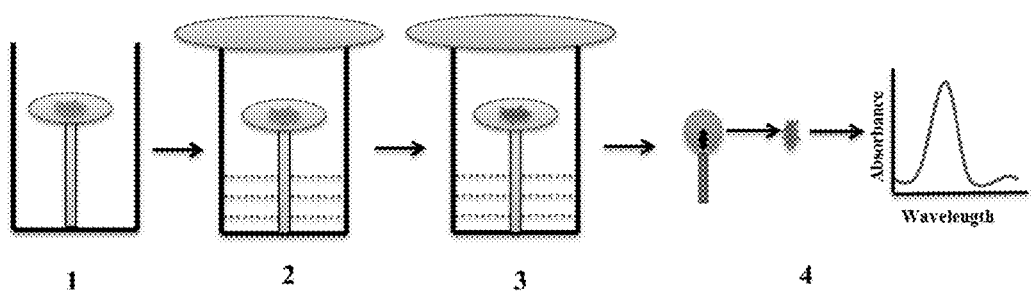

The present invention provides multi-action copper complex of formula X and preparation thereof which are useful for reversible vapochromic detection of polar solvents as well as colorimetric detection of different anions in both aqueous and non-aqueous media.

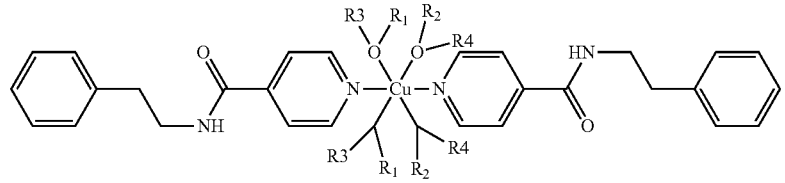

Formula (X)

wherein,
$R_1$, $R_2$, $R_3$ and $R_4$ is selected from H or $R_1$ and $R_3$ jointly represent NO group and $R_2$ and $R_4$ jointly represent NO group.

The present invention provides a multi-action vapochromic copper complexes wherein the representative compounds of Formula X are:
dinitratebis (N-phenethylisonicotinamide)copper(II) of formula (1);

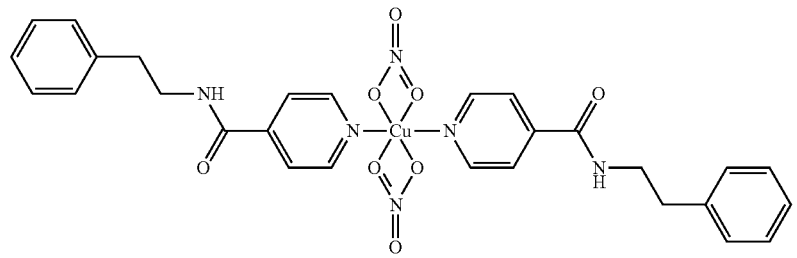

Formula 1 tetraaquabis(N-phenethylisonicotinamide)copper(II)nitrate of formula (2),

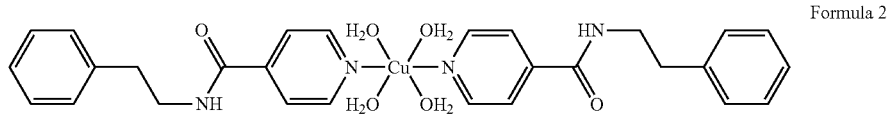

Formula 2

The complex shows vapochromic behavior for polar solvents with colour change occurred within a minute and showed colour change in solid state.

The polar solvents are selected from methanol, ethanol, acetone, dimethylformamide, dimethyl sulfoxide and Tetrahydrofuran.

The complex shows anion sensing capability in the solid state.

The present invention provides novel multi-action metal coordination complexes which are useful for colorimetric detection of anions in both aqueous and non-aqueous media in few seconds.

The present invention provides a process for selective, naked eye detection of anions in aqueous and non-aqueous medium using complex dinitratebis (N-phenethylisonicotinamide)copper(II) of formula (1) or tetraaquabis(N-phenethylisonicotinamide)copper(II)nitrate of formula (2), wherein said process comprises suspending the powder of (1) or (2) in aqueous solution of tetrabutylammonium (TBA) or ammonium salts, alkali metal salts of various anions followed by observing the change in colour of the solid sample within few seconds.

The anions are selected from of chloride, bromide, nitro, thiocynate, formate and acetate.

The present invention provides a process for the synthesis of multi-action copper complex of formula X comprising the steps of:
a. adding triethylamine ($Et_3N$) to a stirred solution of isonicotinoylchloride in Dichloromethane (DCM) at 0° C. followed by addition of 2-phenethylamine and stirring the mixture for 8 hrs at room temperature to obtain N-phenethylisonicotinamide ligand;
b. adding methanolic solution of N-phenethylisonicotinamide ligand of step (a) to $Cu(NO_3)_2 \cdot 3H_2O$ and stirring the reaction mixture followed by refluxing, filtration and then separating the product in two parts (i) and (ii);
c. crystallization of one part of the product of step (b) in methanol to yield blue coloured needle shaped crystals of formula (1) and crystallization of second part of the product of step (b) in a MeOH-water mixture to obtain green coloured plates of formula (2);
d. adding water to the blue crystals of formula 1 to obtain green colour Cu—$H_2O$ formula 2 compound or suspending green crystals of formula 2 in methanol to yield blue crystals of compound Cu-MeOH formula 1.

The present invention provides multi-action copper complex of formula X which shows colorimetric sensing of different geometry anions in aqueous and non-aqueous media within few seconds.

The invention provides products with various anions formed to illustrate the anion sensing properties of complex of formula 1 which are listed in Table 1.

TABLE 1

| Complex of formula 3 (Complex of formula 1 and 2 + Cl anion source) | monoaqua-trichloro-(□2-chloro)-tetrakis(N-phenethylisonicotinamide)-dicopper(II) |

TABLE 1-continued

| Complex of formula 4 (Complex of formula 1 and 2 + Br anion source) | monoaqua-tribromo-(□2-bromo)-tetrakis(N-phenethylisonicotinamide)-dicopper(II) |
| Complex of formula 5 (Complex of formula 1 and 2 + SCN anion source) | di-(N-thiocyanato)-bis(N-phenethylisonicotinamide)copper(II) |
| Complex of formula 6 (Complex of formula 1 and 2 + Formate anion source) | aqua-bis(formato)-bis(N-phenethylisonicotinamide)- copper(II) |
| Complex of formula 7 (Complex of formula 1 and 2+ Acetate anion source) | diaqua-bis(acetato-)-bis(N-phenethylisonicotinamide)-copper(II) |
| Complex of formula 8 (Complex of formula 1 and 2+ Nitrite anion source) | Single crystal could not be grown, however PXRD was recorded |

EXAMPLES

Following examples are given by way of illustration and therefore should not be construed to limit the scope of the invention.

Example 1

Synthesis of N-Phenethylisonicotinamide Ligand

To the stirred solution of isonicotinoylchloride in dry DCM, dry $Et_3N$ (1.1 equivalent) was added drop wise at 0° C. To this reaction mixture, 2-phenethylamine (1.1 equivalents) was added slowly. The reaction mixture was kept stirring for ~8 h at room temperature i.e. at 25° C. DCM was evaporated under reduced pressure to get crude residue to which ethyl acetate was added and sequentially washed with saturated solution of $NaHCO_3$ and brine. The organic layer was dried over solid $Na_2SO_4$ and evaporated in vacuum to get crude product which after column chromatography yielded compound (I).

Complex of formula (1) was synthesized by adding dry methanolic solution of compound I (2.1 equivalent) to $Cu(NO_3)_2 \cdot 3H_2O$ and stirred for 15 minutes. The reaction mixture was then refluxed for ~8 h. The reaction mixture was then filtered to remove unwanted residue and then separated in two parts. The first part (A) was kept for crystallization in the vessel to allow slow evaporation of methanol at room temperature while in the other part (B) equal amount of water was added and kept for crystallization at room temperature i.e. at 25° C. for slow evaporation. Crystallization from part (A) yielded blue coloured needle shaped crystals whereas part (B) produced green coloured plates. The blue crystals (Cu_MeOH, 1) on addition of water turned green (Cu—$H_2O$, 2) while suspension of green crystals in methanol yielded blue crystals within seconds.

Example 2

Figure 3:
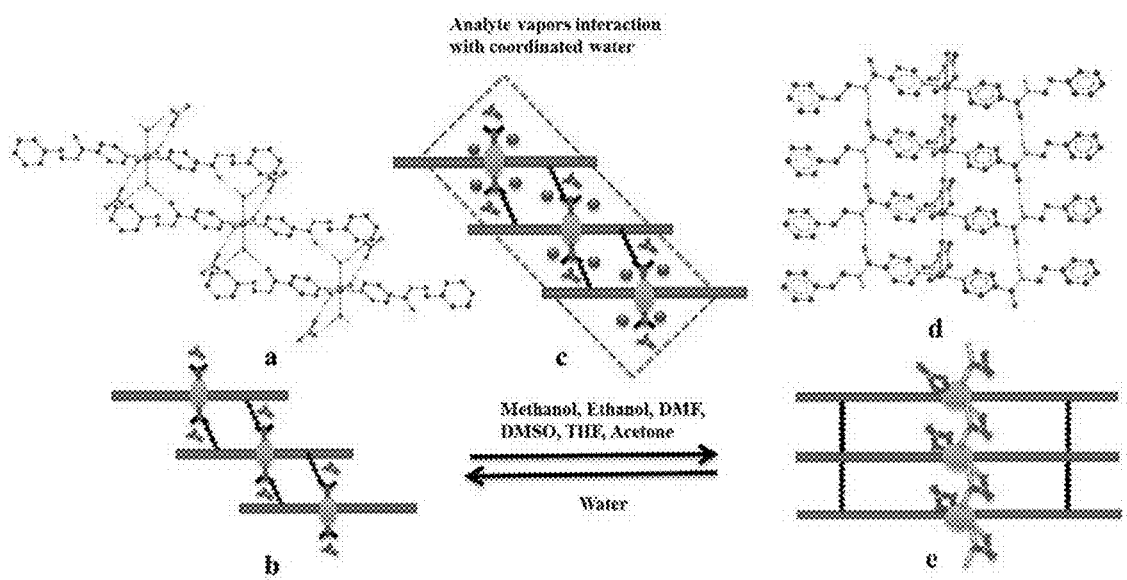
FIG. 3: Schematic representation of mechanism of vapochromism of Complex of formula 1 and 2.

Vapochromic Behavior of 1 and 2: (FIGS. 1 and 3)

Compound 2 was grinded to generate the fine polycrystalline sample that was then spread onto the glass plate. The plate was then placed in crystallization chambers containing solvent. The position of the glass plate in the chamber was much above the solvent upper layer. This crystallization assembly was then covered with glass plate in order to avoid the evaporation of the solvent vapours outside the chamber. After the exposure of the solvent vapours, the green fine crystalline powder of 2 turned blue (1) in methanol, ethanol, acetone, DMF, DMSO and THF vapours. The rate of the change of colour of the crystals was different for different solvents. For example, in methanol solvent, the colour change occurred in few seconds, while in less volatile solvents such as DMSO and DMF, the time taken for naked eye colorimetric change was up to 8-10 h because these solvent are high boiling and less volatile. This vapochromic behaviour is attributed to the electronic state changes and geometrical distortion of Cu(II) coordination sphere. Reversibility of the process was also monitored by keeping blue powder (1) in closed chamber containing water. The colorimetric changes from blue to green (2) revealed the reversible nature of vapochromic phenomenon. No colorimetric change was observed in solvent such as chloroform, dichloromethane, ethylacetate and benzene.

Example 3

Figure 2:
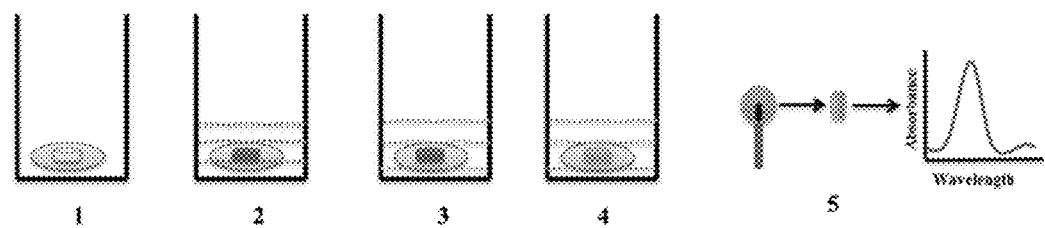
FIG. 2: Anion sensing experiment for compound ($CuH_2O$, 2): (1) green tablet of compound 2, (2) green tablet suspended in methanol, green tablet turned blue within seconds, (3) blue tablet placed in aqueous solution of anions, (4) occurrence of colour change, (5) recording of solid-state UV absorption/reflectance data of tablet.
Figure 4:
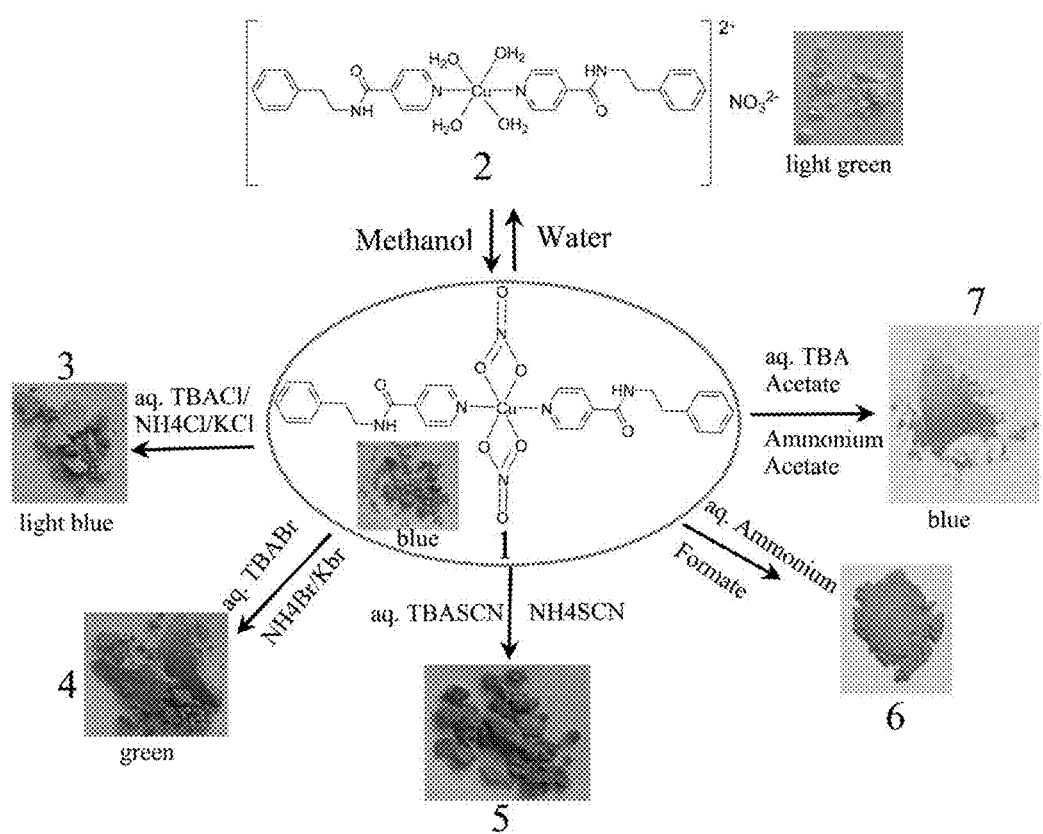
FIG. 4: Schematic representation of anion sensing behaviour of compound 1.
Figure 5:
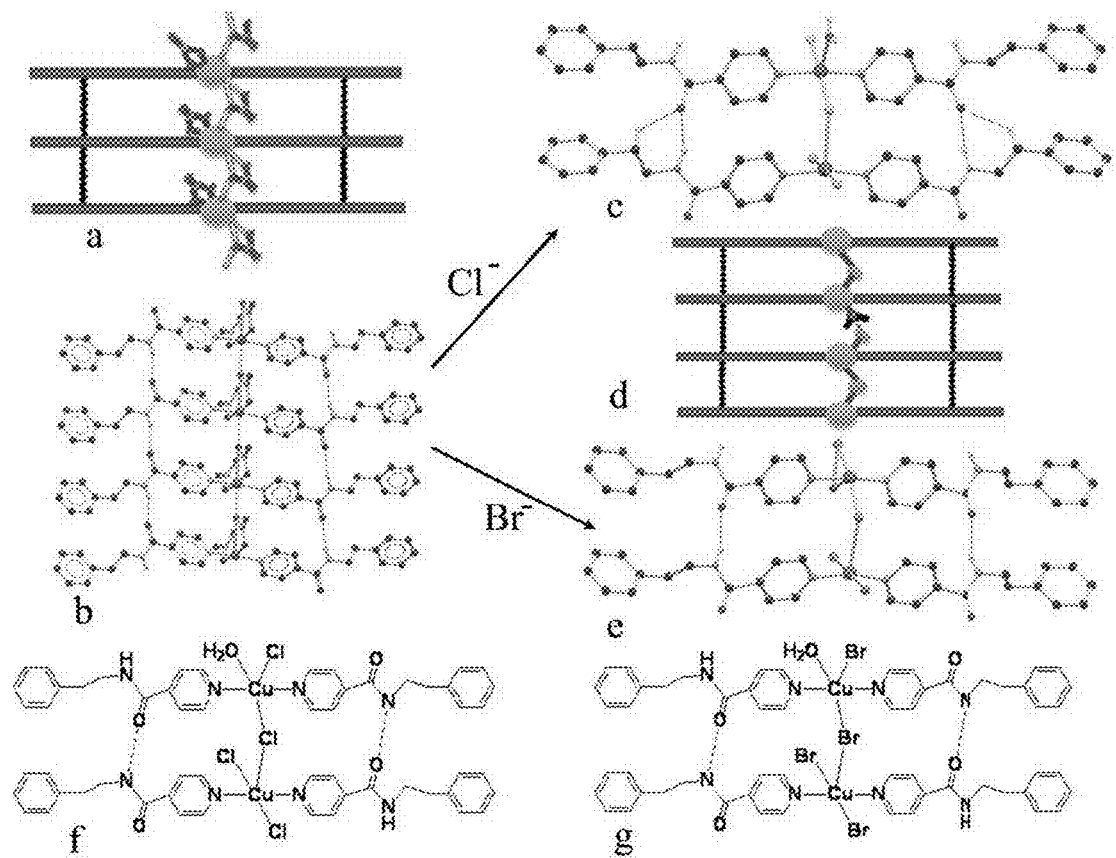
FIG. 5: Schematic illustration of chloride (Compound 3) and bromide (Compound 4) anion sensing mechanism.
Figure 6:
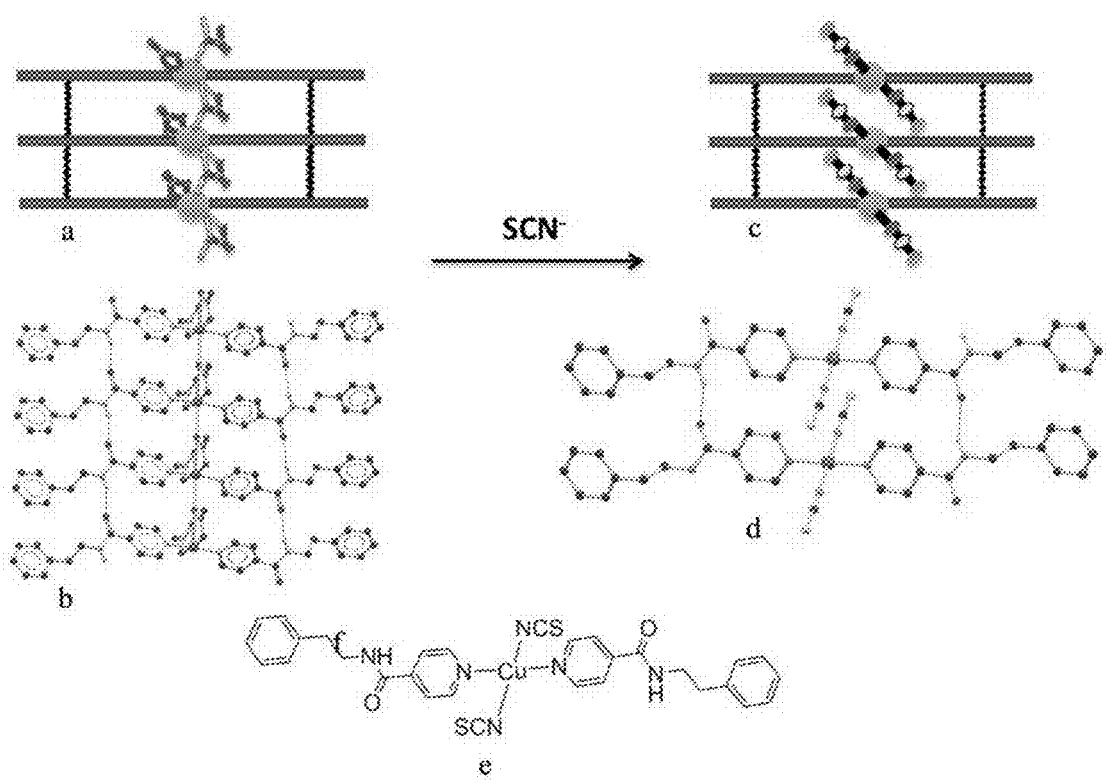
FIG. 6: Schematic illustration of thiocyanate anion sensing mechanism.
Figure 7:
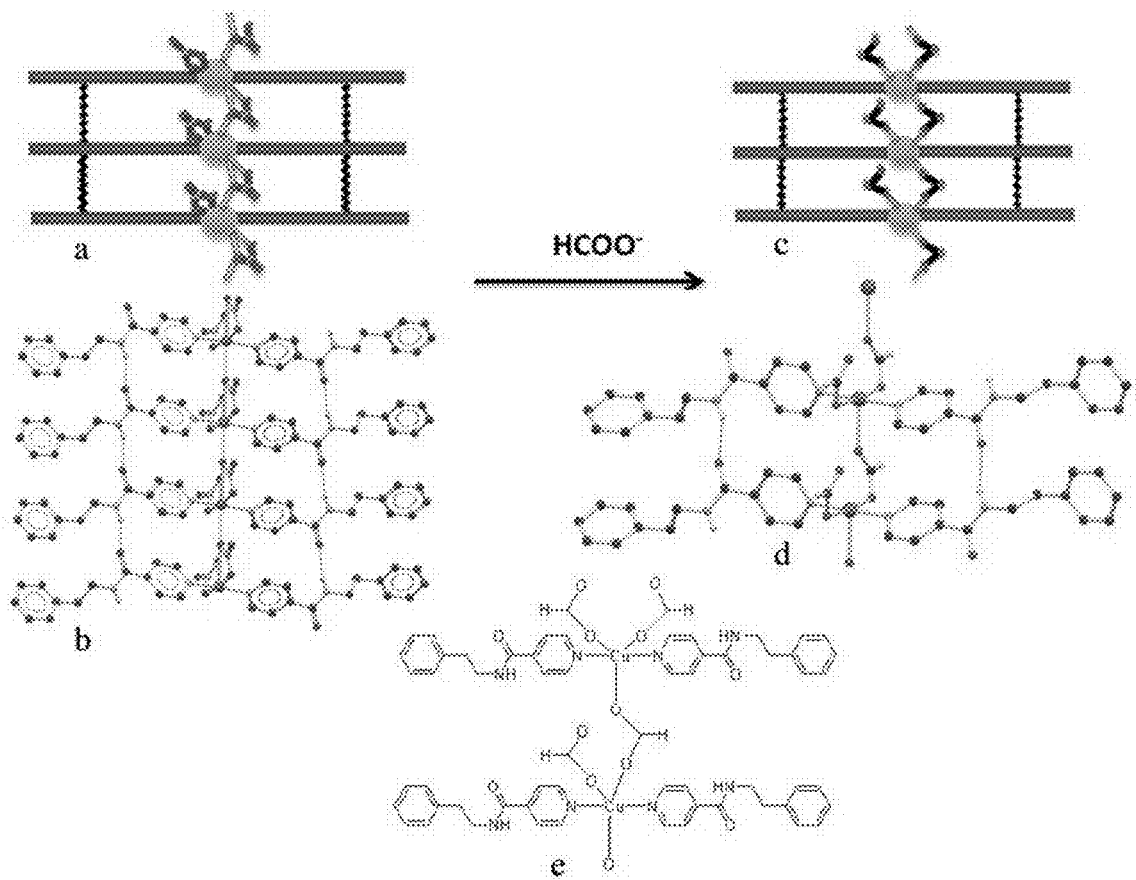
FIG. 7: Schematic illustration of formate anion sensing mechanism.
Figure 8:
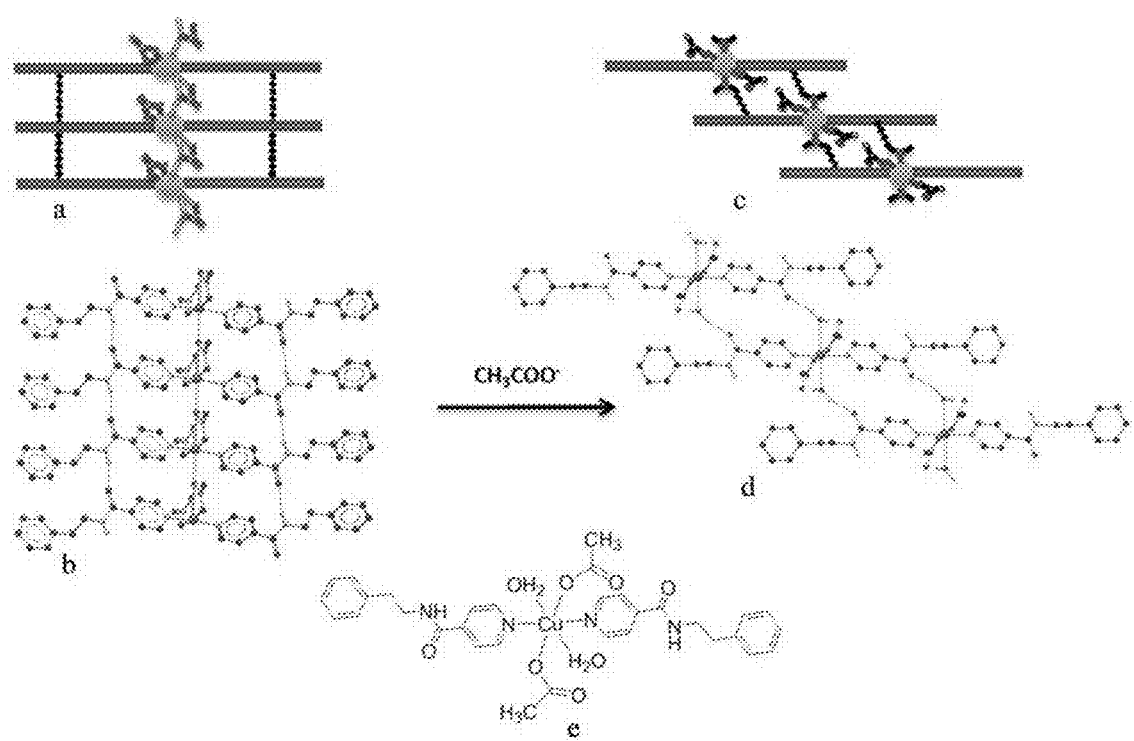
FIG. 8: Schematic illustration of acetate anion sensing mechanism.

Methodology for Anion Sensing Properties of Blue Crystals: (FIGS. 2 and 4)

Cu(II) complex of formula (1) and (2) both revealed anion sensing behavior exhibiting colorimetric change detected by naked eye in few seconds. In comparison to complex of formula (2), complex of formula (1) shows rapid colorimetric detection of anions attributed to faster anion-anion exchange ($NO_3^-$ to X where X: $Cl^-$, $Br^-$, $NO_2^-$, $SCN^-$, $HCOO^-$, $CH_3COO^-$) than $H_2O$-anion exchange ($H_2O$ to X where X: $Cl^-$, $Br^-$, $NO_2^-$, $SCN^-$, $HCOO^-$, $CH_3COO^-$). Based on this observation and reversible switching ability of complex of formula (1) and (2), the following protocol was developed for aqueous detection of anions. The green crystals of (2) was grinded first to generate fine polycrystalline sample which is then suspended in methanol to obtain blue crystallites of Cu(II) complex of formula (1) and subjected to sonication to form fine blue powder. The dry powder of (1) was then pressed to form circular disc which is then suspended in aqueous solution of tetrabutylammonium (TBA) or ammonium salts, alkali metal salts of various anions. The change in colour of the solid sample within a minute from blue to light blue to dark yellowish green was observed depending on the anion sensed by the complex of formula 1. The anion sensing behaviour of complex of formula 1 was confirmed by determining the crystal structure of these complexes (except $NO_2^-$ (8) anions, single crystal of this complex could not be grown). The observed change in the chromogenic properties of complexes is attributed to change in the charge transfer LMCT (Ligand to metal charge transfer), MMCT (metal to metal charge transfer) or d-d transition. Measurement of the PXRD profiles of these complexes and their comparison with simulated PXRD graphs obtained from single crystals XRD showed good match revealing homogeneity of the sample. UV-vis reflectance spectra in solid state were obtained. The solid state UV spectra revealed noticeable $\lambda_{max}$ shift of the UV-vis reflectance spectrum, upon exposure to an analyte.

Example 4

Figure 10:
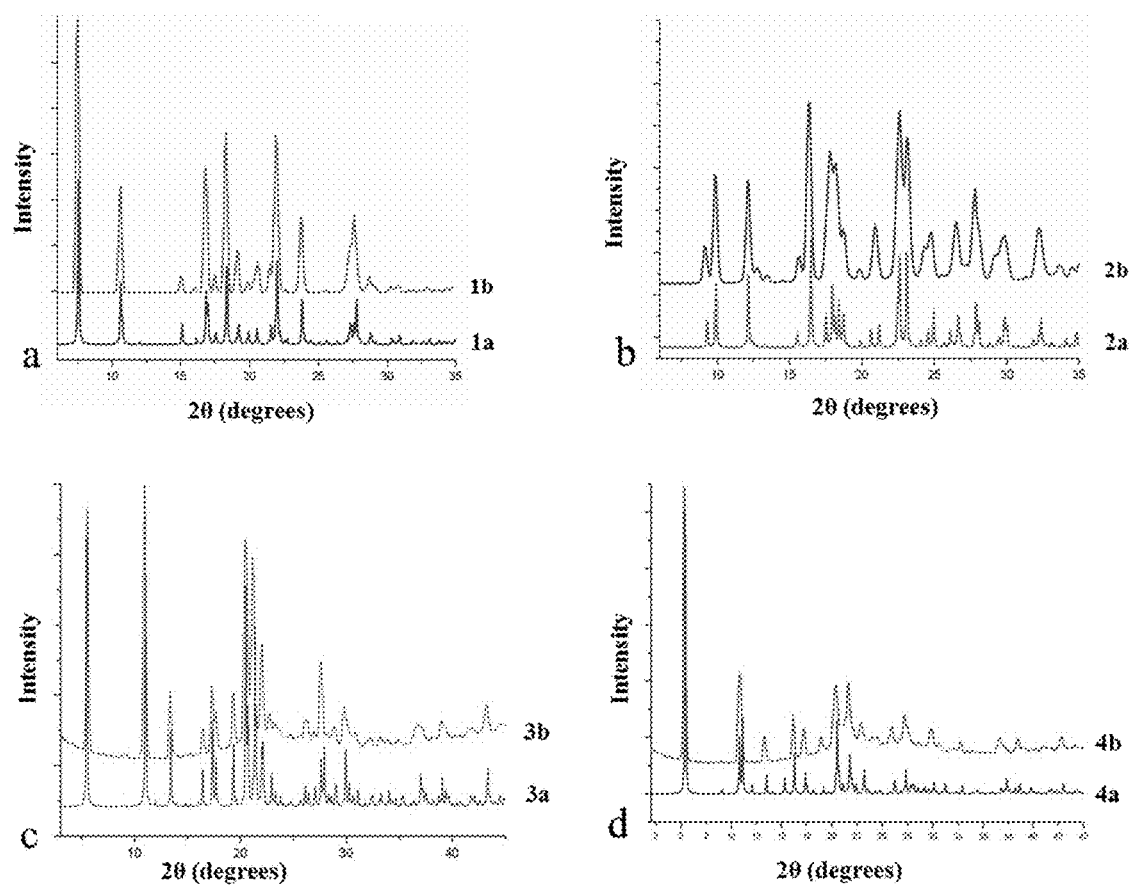
FIG. 10.
Figure 11:
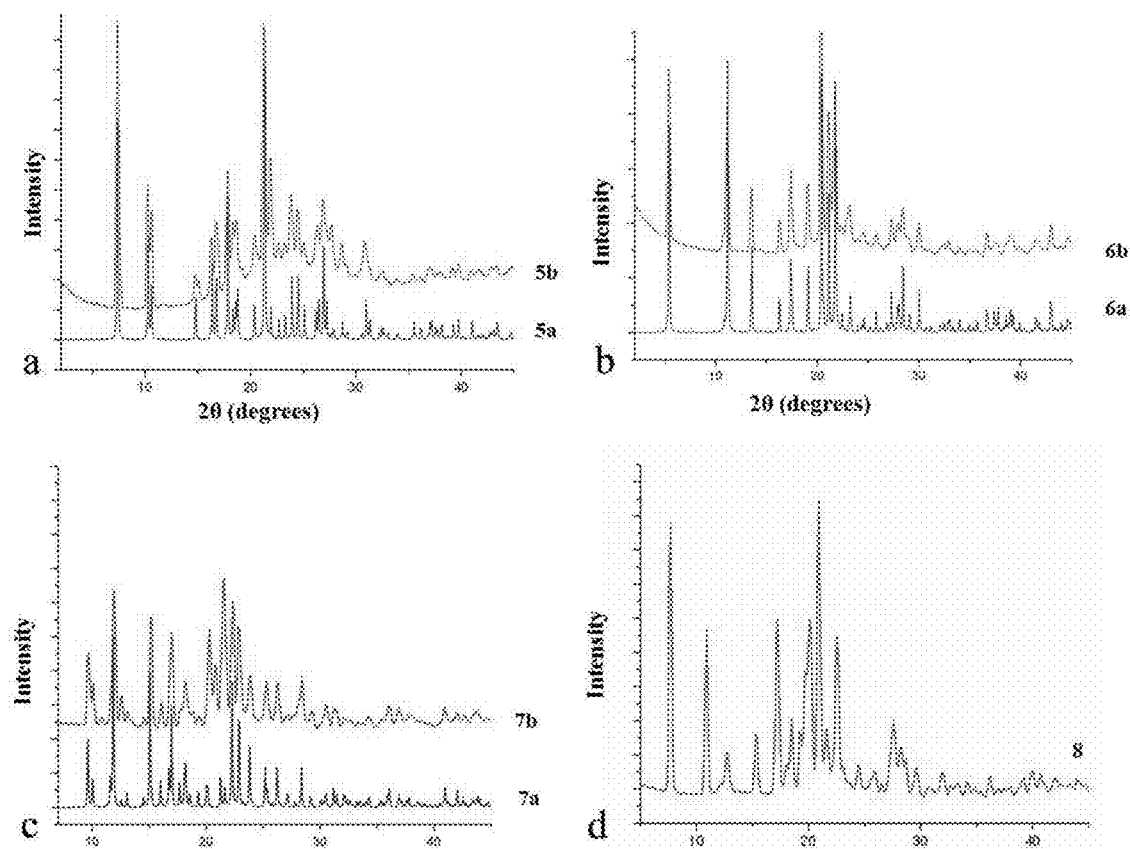
FIG. 11.

Comparative Analysis of Experimental and Simulated PXRD Pattern Obtained from Single Crystal: (FIGS. 10 and 11)

To understand the mechanism of sensing and associated chromogenic change, the aqueous anionic solution of TBAX salts (X:$Cl^-$, $Br^-$, $NO_2^-$, $SCN^-$, $HCOO^-$, $CH_3COO^-$) one equivalent of insoluble blue powder of complex of formula 1 was suspended. After chromogenic change was observed the obtained powder was repeatedly washed with water and powder X-ray diffraction patterns were recorded on Rigaku instrument at continuous scanning rate of 2° 2θ/min using Cu Kα radiation (40 kV, 30 mA) with the intensity of the diffracted X-ray being collected at intervals of 0.1° 2θ. A nickel filter was used to remove Cu $K_\beta$ radiation.

Crystals were grown by suspending the powder into aqueous media from anion sensing experiment as mentioned above and heated till 70° C. in water bath. Sparingly solubilized supernatant was collected and kept for crystallization by slow-cooling method. Simulated powder pattern of single crystal structure analysis matched with collected experimental powder pattern after sensing experiment at room temperature and thus validated illustrated mechanism of anion detection.

Crystal Structure Investigation: (FIGS. 5, 6, 7 and 8)

Single crystal X-ray analysis of compounds 1, 2, 3, 4, 5, 6 and 7 were carried out on a Bruker SMART APEX II single crystal X-ray CCD diffractometer, with graphite-monochromatised (Mo—$K_\alpha$=0.71073 Å) radiation. Crystal structure of 8 (Cu-Nitrite) could not be determined due to poor quality of the crystals. The X-ray generator was operated at 50 kV and 30 mA. Diffraction data were collected with a ω scan width of 0.5° and at different settings of φ and 2θ The sample-to-detector distance was fixed at 5.00 cm. The X-ray data acquisition was monitored by APEX2 program package. All the data were corrected for Lorentz-polarization and absorption effects using SAINT and SADABS programs integrated in APEX2 package. The structures were solved by direct methods and refined by full matrix least squares, based on $F^2$, using SHELX-97. The crystallography data of all the samples is summarized in Table 2.

TABLE 2

| | a (Å) | b (Å) | c (Å) | α (°) | β (°) | γ (°) | V (Å³) | Space group |
|---|---|---|---|---|---|---|---|---|
| Ligand | 8.312(1) | 5.189(1) | 28.456(1) | 90 | 96.440(1) | 90 | 1219.46 | $P2_1/n$ |
| Cu_MeOH (1), nitrate complex | 5.109(1) | 16.644(1) | 16.645(1) | 90 | 98.30(1) | 90 | 1400.61 | $P2_1$ |
| Cu_H₂O (2), water complex | 8.106(1) | 19.032(1) | 10.426(1) | 90 | 104.109(1) | 90 | 1559.87 | $P2_1/n$ |
| Cu(II)-Chloride (3) | 8.304(1) | 32.290(2) | 10.127(1) | 90 | 90.00 | 90 | 2715.14 | $P2_1/m$ |
| Cu(II)-Bromide (4) | 8.277(1) | 32.574(4) | 10.174(2) | 90 | 90.001(8) | 90 | 2743.02 | $P2_1/m$ |
| Cu(II)-Thiocyanate (5) | 5.113(1) | 16.664(2) | 17.680(1) | 90 | 103.78(1) | 90 | 1462.88 | $P2_1/c$ |

TABLE 2-continued

| | a (Å) | b (Å) | c (Å) | α (°) | β (°) | γ (°) | V (Å³) | Space group |
|---|---|---|---|---|---|---|---|---|
| Cu(II)-Formate (6) | 5.131(1) | 16.312(3) | 33.050(4) | 90 | 98.931(2) | 90 | 2732.64 | P2$_1$/c |
| Cu(II)-Acetate (7) | 8.62(1) | 18.36(2) | 10.59(2) | 90 | 108.52(2) | 90 | 1588.23 | P2$_1$/n |

Figure 9:
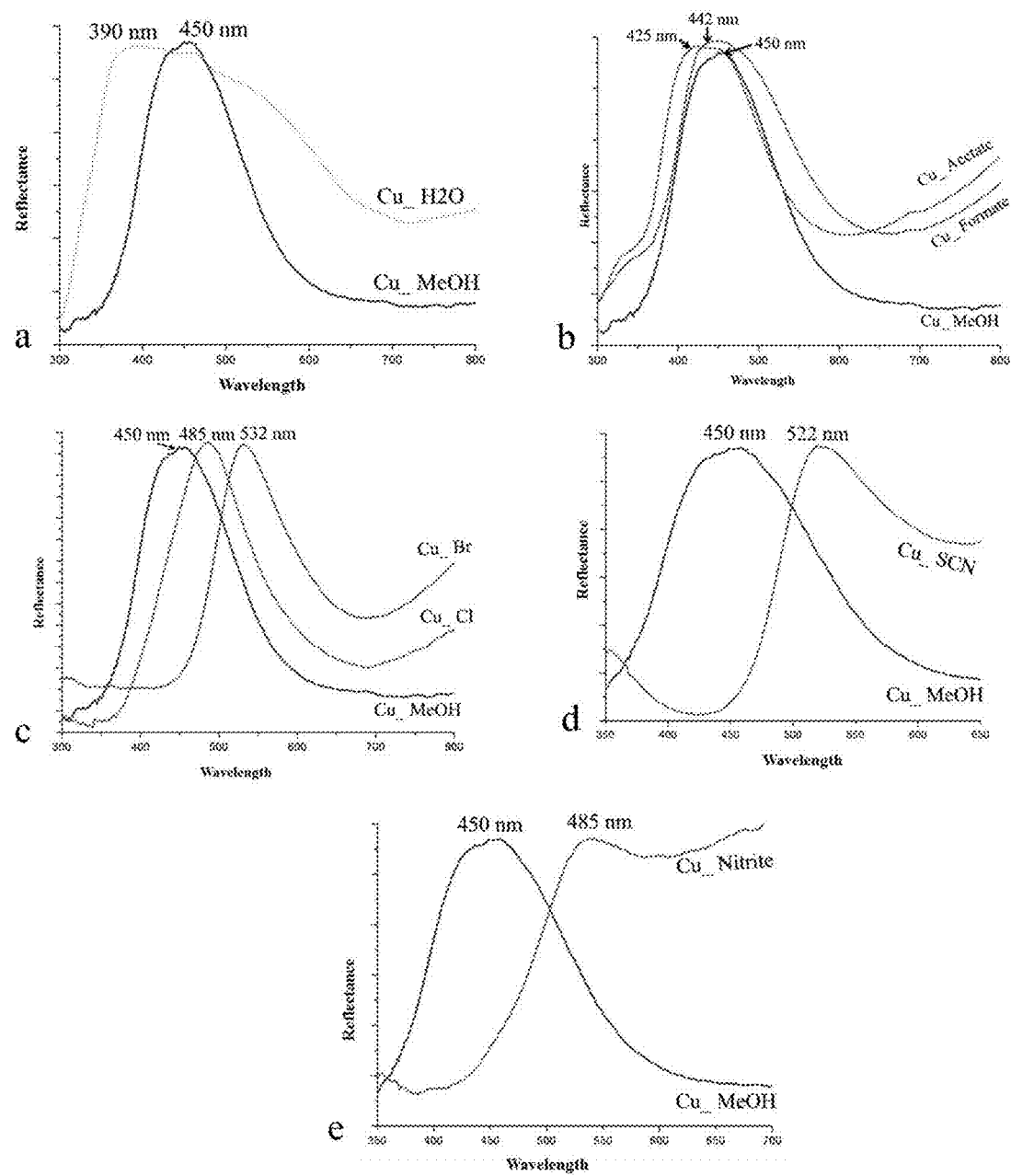
FIG. 9: Solid state UV reflectance spectra of the solid material FIG. 9(a) vapochromic detection of methanol vapors (Cu_$H_2O$ to Cu_MeOH).

Comparative Analysis of Solid State UV Reflectance Spectra of Starting Cu_MeOH (1) and Final Experimental Solid Material of Vapochromism or Anion Sensing Experiment: (FIG. 9)

The reflectance spectra of the samples were measured by using Jasco UV-Vis spectrophotometer (V570 UV-VIS-NIR. The reflectance $\lambda_{max}$ are mentioned in Table 3.

TABLE 3

| Compound | Reflectance $\lambda_{max}$ (nm) |
|---|---|
| Complex of formula 1 (Cu_MeOH) | 450 |
| Complex of formula 2 (Cu_H$_2$O) | 390 |
| Complex of formula 3 (1 + Cl) | 485 |
| Complex of formula 4 (1 + Br) | 532 |
| Complex of formula 5 (1 + SCN) | 522 |
| Complex of formula 6 (1 + Formate) | 442 |
| Complex of formula 7 (1 + Acetate) | 425 |
| Complex of formula 8 (1 + Nitrite) | 538 |

Example 5

Naked Eye Detection of Anions Via Grinding

So far the use the complex of formula 2 for sensing polar solvent vapors and anions in competent aqueous media was explored but peculiar features is its ability to differentiate between various salts by simple grinding. Although many methods are available in the market for removal or discrimination of various salts such as anion exchange chromatography but they are laborious and expensive.

Figure 12:
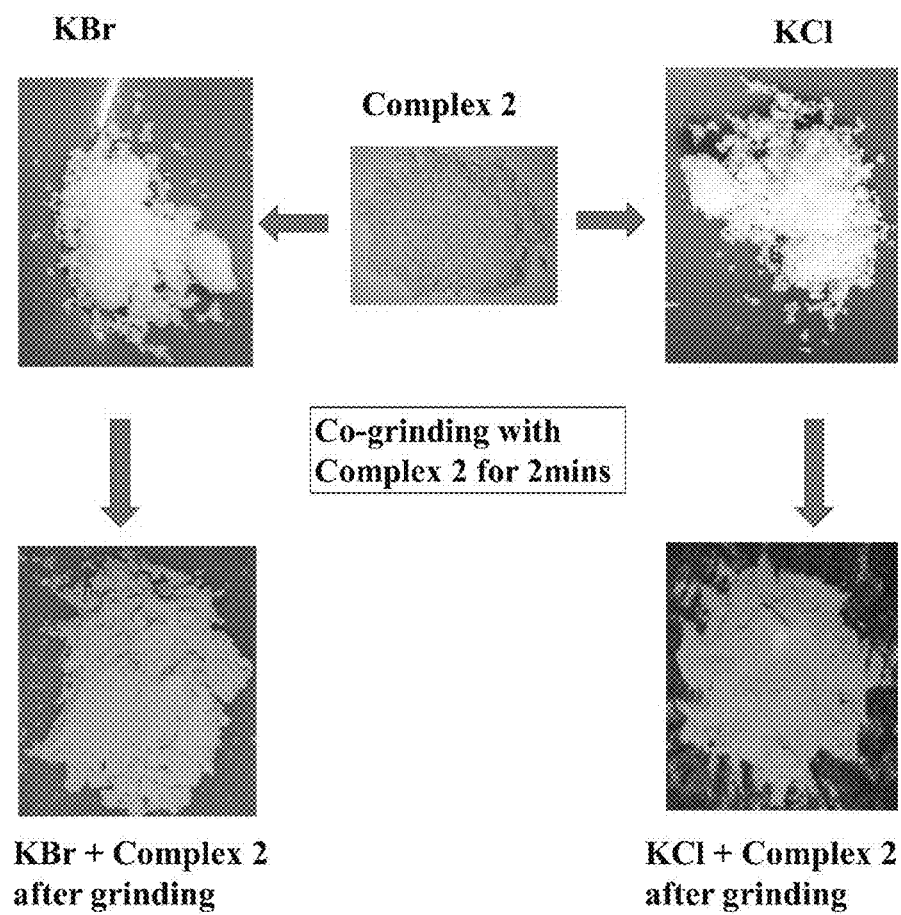
FIG. 12. Cogrinding experiment of complex of formula 2 (light green) with KBr (colourless) and KCl (colourless) showing colour change to dark green and blue respectively.

Co-grinding of particular potassium/sodium salts of Cl⁻, Br⁻, NO$_2$⁻, SCN⁻, HCOO⁻, CH$_3$COO⁻ with 20:1 ratio for 2-5 minutes imparts corresponding colour to the solid material as shown in table 3. We have demonstrated use of complex of formula 2 for differentiating between potassium salt of chloride and bromide by grinding method (FIG. 12). The anion exchange take place on grinding the complex of formula 2 with the KBr and KCL salt which gives rise to the colour change.

Advantages of Invention

Solid state detection and can be used in the form of film or tablet.
Detection in aqueous as well as non-aqueous media.
Fast detection of anions, Cost-effective.
Highly sensitive and ability to detect low concentration of anions.
Covers broad spectrum of anions from monovalent halides to larger anions such as acetate.
Detection via visible colour changes.

We claim:

1. A complex of formula X

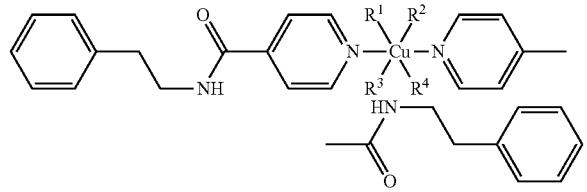

Formula X

Wherein R$_1$, R$_2$, R$_3$ and R$_4$ is selected from H$_2$O or NO$_3$; Provided that when R$_1$, and R$_3$ is NO$_3$ then R$_2$ and R$_4$ is absent.

2. The complex as claimed in claim 1, wherein representative compound of formula X are

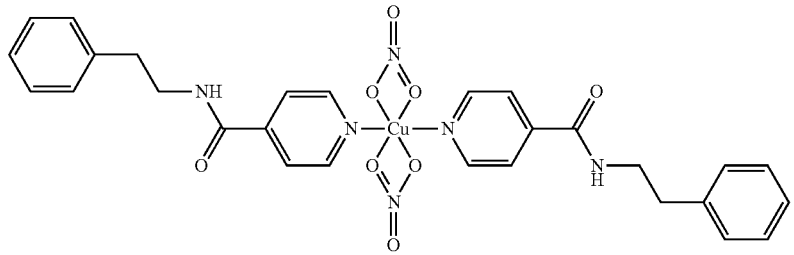

Formula 1 and

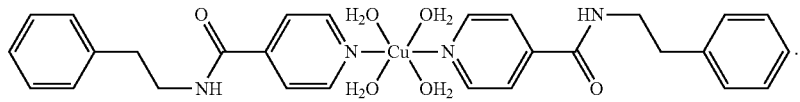

Formula 2

3. The complex as claimed in claim 1, wherein said complex shows vapochromic behavior for polar solvent within a minute.

4. The complex as claimed in claim 3, wherein the polar solvent is selected from the group consisting of methanol, ethanol, acetone, dimethylformamide, dimethyl sulfoxide and Tetrahydrofuran.

5. The complex as claimed in claim 1, wherein said complex showed colour change in the solid state.

6. A process for the synthesis of complex of formula X as claimed in claim 2 the said process comprising the steps of:
   a. adding triethylamine ($Et_3N$) to a stirred solution of isonicotinoylchloride in dichloromethane (DCM) followed by adding 2-phenethylamine with stirring for period in the range of 7 to 8 hrs at room temperature in the range of 20 to 30° C. to obtain N-phenethylisonicotinamide ligand;
   b. adding methanolic solution of N-phenethylisonicotinamide ligand of step (a) to $Cu(NO_3)_2 \cdot 3H_2O$ with stirring followed by refluxing, filtering and separating the solution in two parts;
   c. crystallizing one part of the solution as obtained in step (b) in methanol to yield blue coloured needle shaped crystals of complex of formula (1) and crystallizing the second part of the solution as obtained in step (b) in a MeOH-water mixture to obtain green coloured plates of complex of formula (2);
   d. adding water to the blue crystals of formula 1 to obtain green crystal of formula 2 and suspending green crystals of formula 2 in methanol to yield blue crystals of formula 1.

7. A process for selective, naked eye detection of anions in aqueous and non-aqueous medium using complex of formula X of claim 1 comprising the steps of:
   i. suspending the powder of complex of formula X in aqueous solution of tetrabutylammonium (TBA) or ammonium salts, alkali metal salts of various anions in the ratio 20:1 followed by observing the change in colour of the solid sample.

8. The process as claimed in claim 7, wherein the anions are selected from the group consisting of chloride, bromide, nitro, thiocynate, formate and acetate.

9. The process as claimed in claim 7, wherein said process may comprises co-grinding the powder of complex of formula X with tetrabutylammonium (TBA) or ammonium salts, alkali metal salts of various anions for period in the range of 2 to 5 minutes followed by observing the change in colour of the solid sample.

* * * * *